United States Patent [19]
Looney

[11] Patent Number: 5,876,332
[45] Date of Patent: Mar. 2, 1999

[54] SURGICAL SUPPORT MEMBER

[75] Inventor: Christopher S. Looney, Roswell, Ga.

[73] Assignee: Genzyme Corporation, Framingham, Mass.

[21] Appl. No.: 899,934

[22] Filed: Jul. 24, 1997

[51] Int. Cl.[6] ................................................. A61B 11/02
[52] U.S. Cl. .......................................... 600/227; 600/102
[58] Field of Search ................................ 600/102, 227, 600/228, 229, 230; 248/278.1, 279.1, 422; 285/166; 269/909, 74, 75, 61

[56] References Cited

U.S. PATENT DOCUMENTS

| | | | |
|---|---|---|---|
| 4,355,631 | 10/1982 | LeVahn | 600/230 |
| 4,457,300 | 7/1984 | Budde | 128/20 |
| 4,949,707 | 8/1990 | LeVahn et al. | 128/20 |
| 5,154,723 | 10/1992 | Kubota et al. | 600/102 X |
| 5,167,223 | 12/1992 | Koros et al. | 128/20 |
| 5,571,072 | 11/1996 | Kronner | 600/102 |
| 5,609,565 | 3/1997 | Nakamura | 600/102 X |
| 5,704,900 | 1/1998 | Dobrovolny et al. | 600/227 X |

FOREIGN PATENT DOCUMENTS 2 233 561  1/1991  United Kingdom .

*Primary Examiner*—Beverly M. Flanagan
*Attorney, Agent, or Firm*—Needle & Rosenberg, P.C.

[57] ABSTRACT

An apparatus for mounting a surgical instrument to a stationary member comprising an arm adapted to support the surgical instrument, a mounting member fixedly attached to the stationary member, and a rotatable positioning segment for coupling the arm to the mounting member so that the arm is rotatable to a selected one of a plurality of desired radial positions relative to the mounting member and is detachably coupled to the mounting member in the desired radial position.

16 Claims, 5 Drawing Sheets

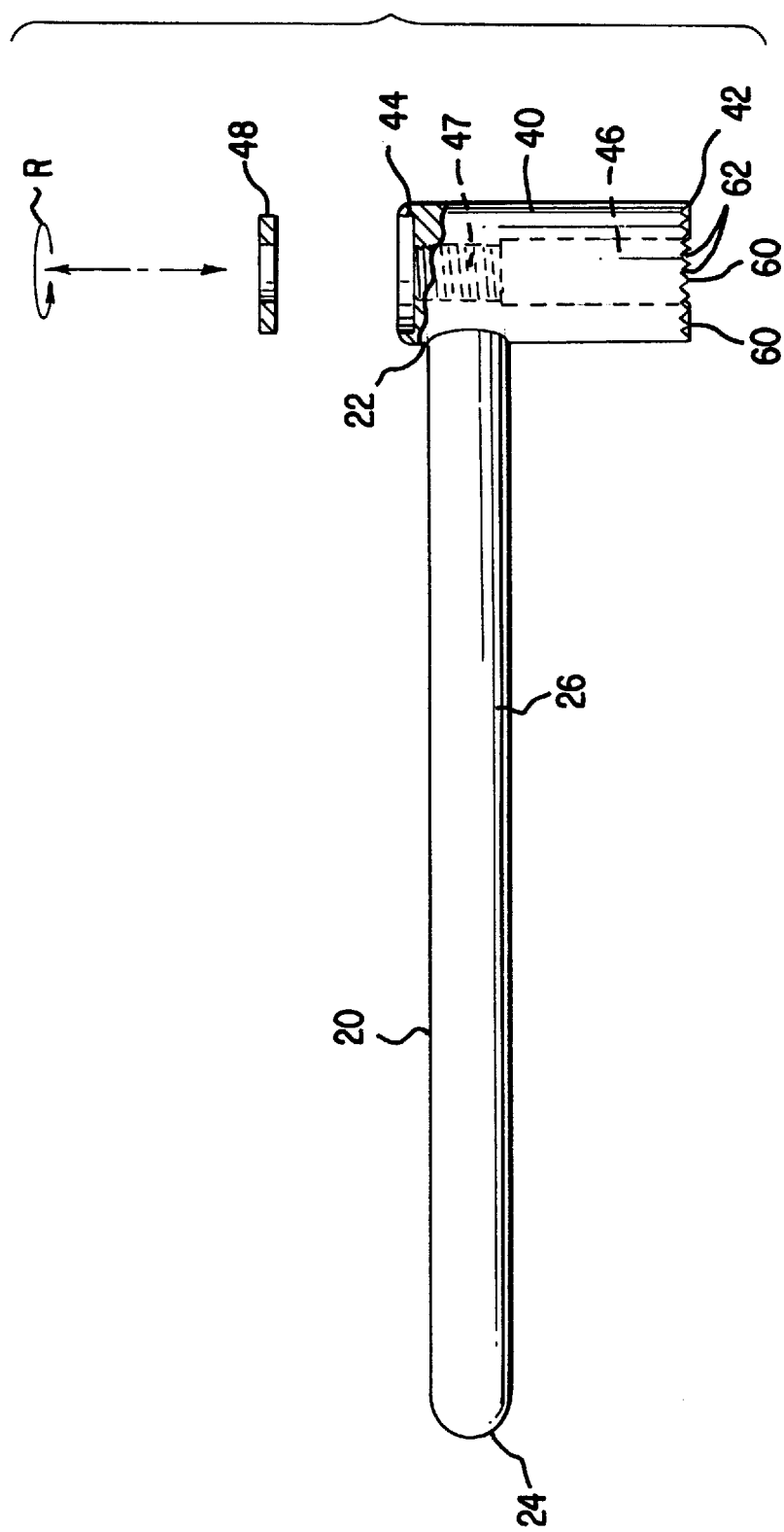

SURGICAL SUPPORT MEMBER

BACKGROUND OF THE INVENTION

1. Field of the Invention

This invention relates to an apparatus used for locating and supporting a surgical instrument to enable a surgeon flexibility in performing a surgical procedure at the surgical site and, more particularly, to an apparatus adapted to movably connect the surgical instrument to a stationary member, such as a rib retractor, which is already being used in the procedure.

2. Background Art

Atherosclerosis or coronary artery disease is among the most common and serious health problems today. Surgical correction of occluded or stenosed coronary arteries via bypass grafting through conventional approaches, such as the sternotomy, are probably the most common procedure currently used, especially where multiple bypass grafts are needed. Conventional bypass graft surgery requires that the heart be stopped and the patient placed on a heart/lung bypass machine, which occurs at considerable expense and risk to the patient.

In an effort to reduce the expense, risk, and trauma to the patient, physicians have recently used minimally invasive surgical approaches to operate on the heart, such as intercostal and endoscopic access to the surgical site. In recent years interventional techniques, such as percutaneous transluminal angioplasty (PTCA), have gained popularity. The transluminal approach is a minimally invasive technique which occurs on a beating heart, thus eliminating the expense and risk of stopping the heart, circumventing the heart/lung bypass machine, and decreasing patient recovery time.

Prior to the present invention, attempts at performing minimally invasive bypass grafting on a beating heart have been hindered by the lack of adequate access through a reduced surgical field. Space is very limited, particularly for minimally invasive procedures. Overcoming this drawback better enables minimally invasive bypass grafting to be performed, thus avoiding the associated problems with conventional bypass graft surgery.

SUMMARY OF THE INVENTION

The above drawbacks of the prior art are overcome by the present invention, which is a surgical support member comprising an arm, a mounting member, and a means for coupling the arm to the mounting member. The present invention is used to rotatably connect a surgical instrument to a stationary member to allow the surgeon to position the surgical instrument to provide the greatest access to the surgical site. It is preferred that the stationary member be equipment already in use in the surgical procedure, such as a rib retractor.

The arm is adapted to support the surgical instrument, such as a stabilizer for stabilizing the beating heart. The mounting member of the present invention is fixedly attached to the stationary member, such as a rib retractor. A feature of the present invention is that the stationary member preferably has more than one mounting member so that the surgeon has a choice of multiple locations to couple the arm to the stationary member. And, since the arm is rotatable relative to the mounting member and the stationary member, the arm and surgical instrument that it supports can be rotated to an out of the way position to provide better access to the surgical site.

The coupling means joins the connecting end of the arm to the mounting member. The coupling means also allows the arm to rotate to a selected one of a plurality of desired radial positions relative to the mounting member and then be secured at the desired location. In the preferred embodiment, the coupling means comprises a positioning segment and a means for detachably securing the positioning segment to the mounting member in the desired radial position. The positioning segment has a first end adapted to be disposed adjacent the mounting member and an opposite second end. The positioning segment rotates relative to the mounting member about an axis of rotation. The positioning segment also preferably defines a bore extending along and surrounding the axis of rotation. A portion of the positioning segment intermediate its first and second ends is attached to the connecting end of the arm.

The detachable securing means preferably comprises a rod having an exterior surface, a bottom end, and a top end. At least a portion of the exterior surface of the rod is of a size to be complementarily received into the bore. A portion of the top end of the rod is wider than the bore.

The mounting member defines a passage through at least a portion thereof. The passage is of a size to complementarily receive a portion of the rod adjacent its bottom end. The passage and portion of the exterior surface of the rod adjacent its bottom end preferably have complementary threaded surfaces so that the rod is movable within the passage by rotating the rod relative to the mounting member.

The positioning segment can be placed in one of two operative positions relative to the mounting member, which are an engaged position and a released position. In the engaged position, the rod is positioned within the passage of the mounting member a desired depth so that a portion of the top end of the rod contacts a portion of the second end of the positioning segment. The first end of the positioning segment concurrently contacts the engaging surface of the mounting member so that the positioning segment is held between the mounting member and the top end of the rod. In the released position, the top end of the rod is spaced apart from the second end of the positioning segment so that the positioning segment is rotatable from one desired radial position to another desired radial position.

Additionally, the detachable securing means preferably further comprises a means for locking the positioning segment at the selected desired radial position when in the engaged position. The preferred locking means comprises the first end of the positioning segment having a non-planar surface and the engaging surface of the mounting member having a complementary non-planar surface. Thus, when the non-planar surfaces of the positioning segment and the mounting means contact each other when in the engaged position, they prevent radial movement between the positioning segment and the mounting member.

Thus, it is an object of the invention to provide an apparatus for supporting a surgical instrument for surgery on a predetermined area of the heart or other organ of a patient to enable a surgeon to perform a surgical procedure at the predetermined site. Another object of the invention is to provide an apparatus as above that is adapted for rotational attachment to a stationary member that provides better access to the surgical site. The objects of the invention, however, are not intended to limit the use of the invention. These and other objects of the invention will be apparent to the skilled artisan based upon the following disclosure.

BRIEF DESCRIPTION OF THE FIGURES OF THE DRAWINGS

FIG. 3 is a side view of the arm and the positioning segment shown in FIG. 1.

DETAILED DESCRIPTION OF THE INVENTION

Figure 1:
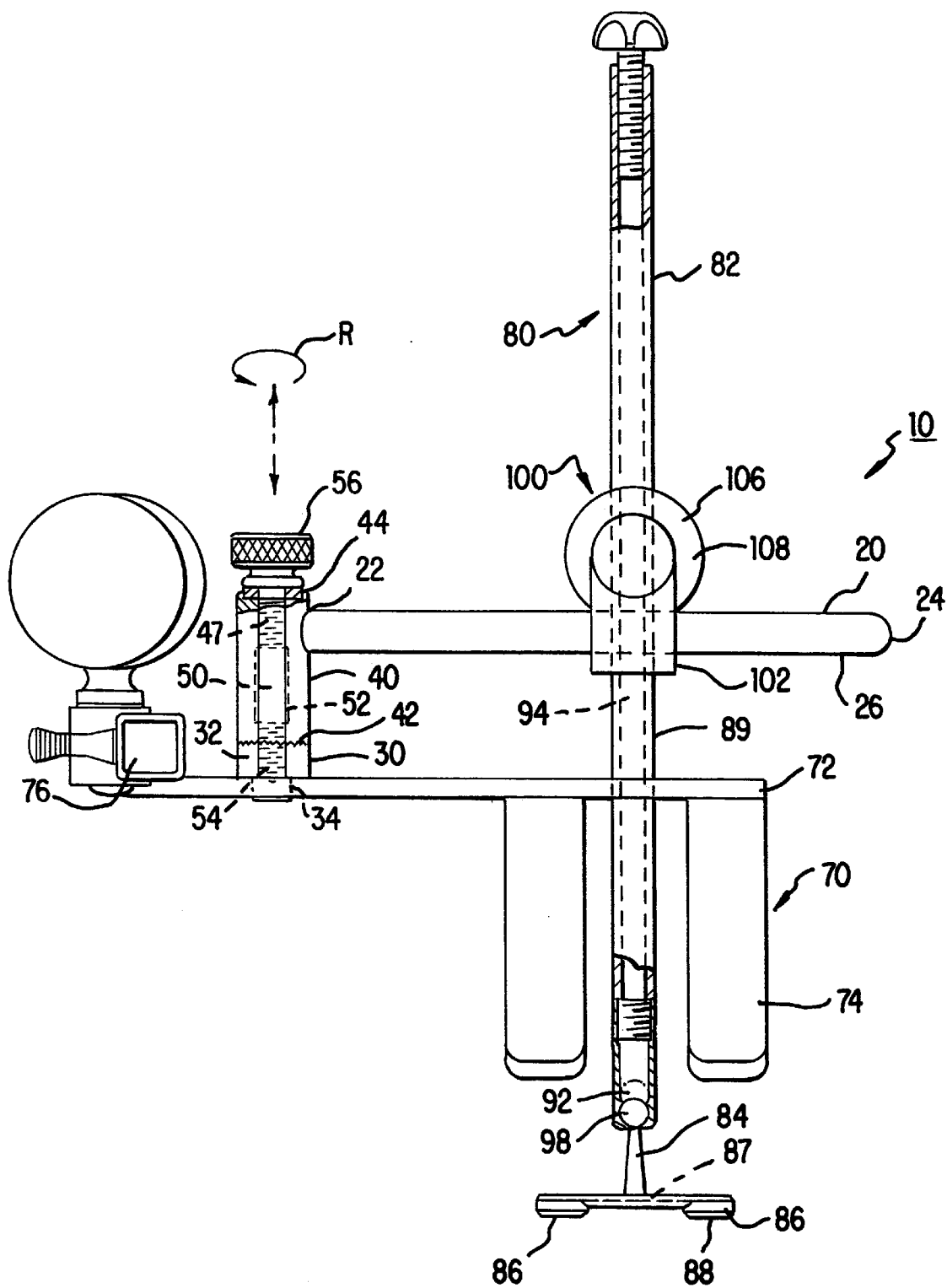
FIG. 1 is a front view of one embodiment of the present invention showing a stabilizer mounted to the arm and the mounting member attached to a rib retractor.

The present invention is more particularly described in the following examples that are intended as illustrative only since numerous modifications and variations therein will be apparent to those skilled in the art. As used in the specification and in the claims, "a" can mean one or more, depending upon the context in which it is used. The preferred embodiment is now described with reference to the figures, in which like numbers indicate like parts throughout the figures.

As shown in FIGS. 1–5, the present invention, a surgical support member 10, comprises an arm 20, a mounting member 30, and a means for coupling the arm 20 to the mounting member 30. The present invention is used to connect a surgical instrument 80 to a stationary member 70 to allow the surgeon to position the surgical instrument 80 to provide the greatest access to the surgical site.

The arm 20 has a connecting end 22, an opposed free end 24, and a body portion 26 extending therebetween. In the preferred embodiment, the body portion 26 of the arm 20 is an elongated segment that has a circular cross section. The body portion 26 of the arm 20 is adapted to support the surgical instrument 80. An example of a surgical instrument 80 is a stabilizer 82, which is discussed in more detail below. Other examples of surgical instruments include light sources, carbon dioxide misting devices, and other retractors, such as mitro valve retractors and the like.

Figure 2:
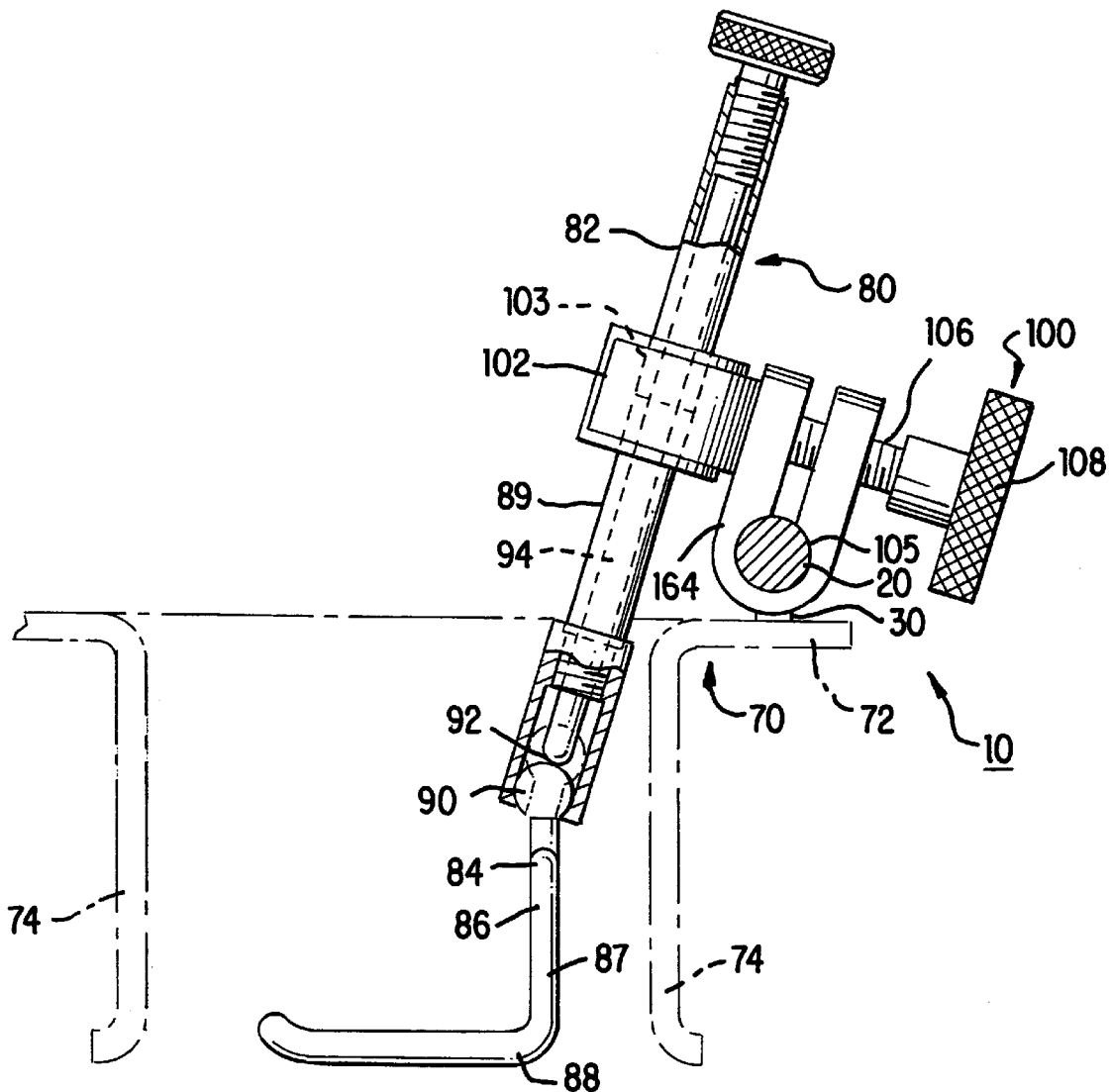
FIG. 2 is a side view of FIG. 1.
Figure 5:
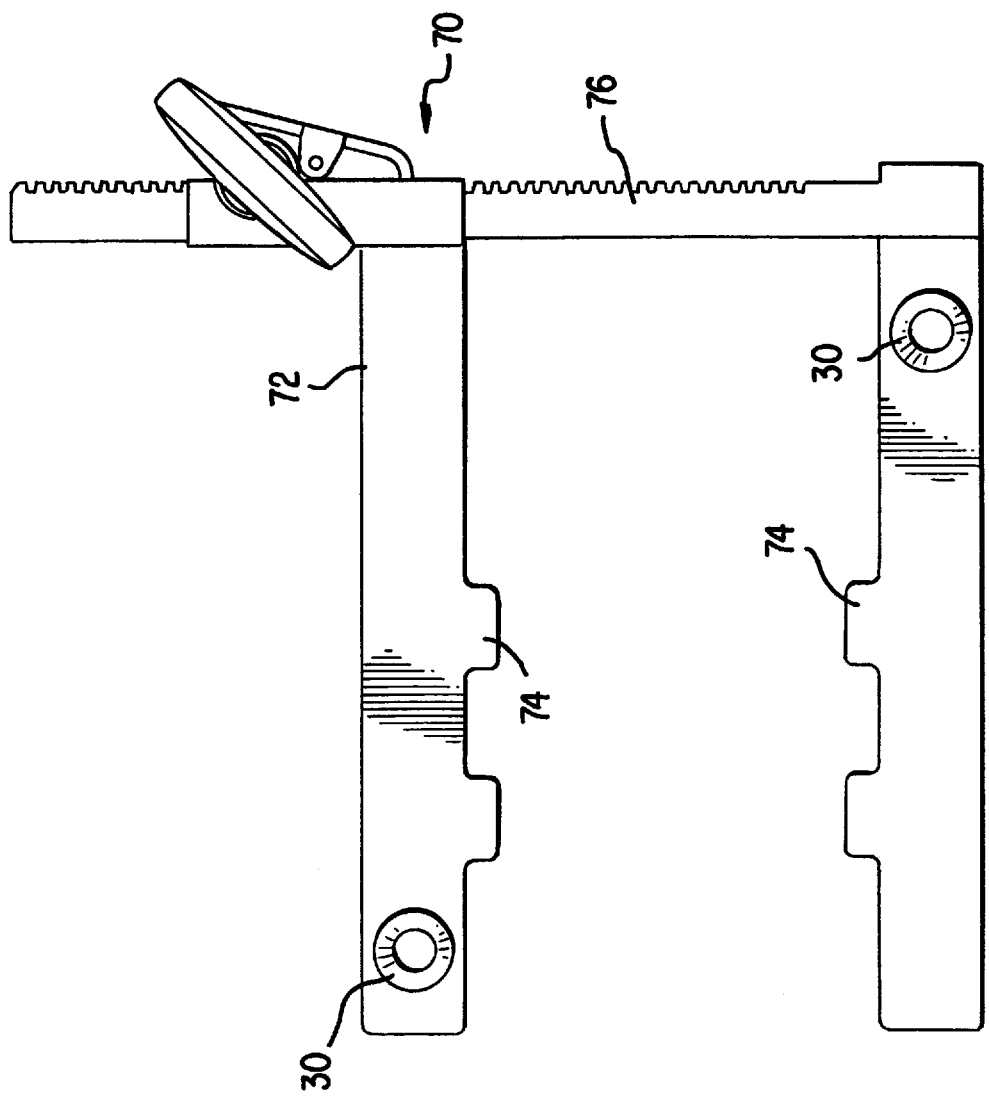
FIG. 5 is a top plan view of a rib retractor used in conjunction with the present invention, in which two mounting members are fixedly attached to the rib retractor.

The mounting member 30 of the present invention is fixedly attached to the stationary member 70, an example of which is a rib retractor 72 as shown in FIGS. 1, 2, and 5. Other examples of stationary members include a table and the like.

Figure 4B:
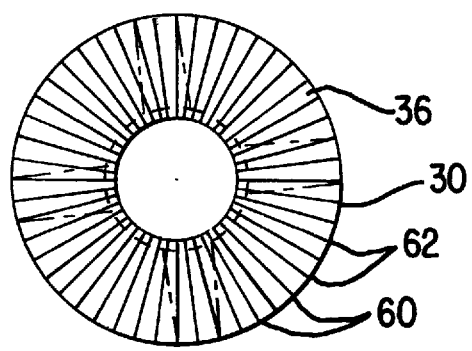
FIG. 4B is a top plan view of FIG. 4A.
Figure 4A:
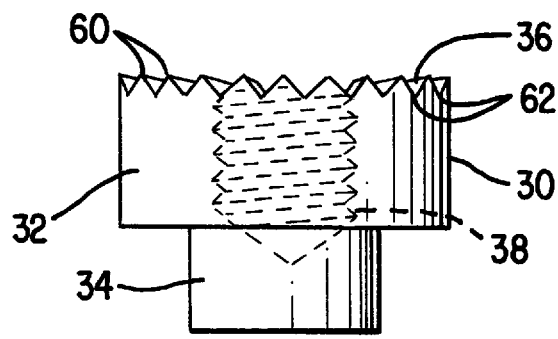
FIG. 4A is a side view of mounting member shown in FIG. 1.

Referring to FIGS. 4A and 4B, the mounting member 30 has an upper portion 32, a lower portion 34, and an engaging surface 36. The upper portion 32 is wider than the lower portion 34. Preferably, the lower portion 34 is disposed into a hole in the stationary member 70, as shown in FIG. 1. The preferred embodiment uses a weld (not shown) to attach the mounting member 30 to the stationary member 70.

A feature of the present invention is that the stationary member 70 preferably has more than one mounting member 30 so that the surgeon has a choice of multiple locations to couple the arm 20 to the stationary member 70. Referring to FIG. 5, two mounting members 30 are attached to the rib retractor 72 in a caddy corner orientation.

The coupling means joins the connecting end 22 of the arm 20 to the mounting member 30. The coupling means also allows the arm 20 to rotate to a selected one of a plurality of desired radial positions relative to the mounting member 30 and then be secured at the desired location. That is, the arm 20 is rotatable to the desired radial position and then the coupling means detachably couples the arm 20 to the mounting member 30 when the arm 20 is properly oriented.

In the preferred embodiment, the coupling means comprises a positioning segment 40 and a means for detachably securing the positioning segment 40 to the mounting member 30 in the desired radial position. The positioning segment 40 has a first end 42 adapted to be disposed adjacent the engaging surface 36 of the mounting member 30 and an opposite second end 44. The positioning segment 40, as best shown in FIGS. 1 and 3, rotates relative to the mounting member 30 about an axis of rotation R. The positioning segment 40 also preferably defines a bore 46 extending along and surrounding the axis of rotation R. A portion of the bore 46 adjacent the second end 44 is threaded, which is referred to as the threaded section 47 of the bore 46. Referring to FIG. 3, a top piece 48 can optionally be fixedly attached to the second end 44 of the positioning segment 40 for separating the second end 44 and a portion of the rod 50 (discussed below), which are preferably formed of similar materials to prevent seizing.

A portion of the positioning segment 40 intermediate its first and second ends 42, 44 is attached to the connecting end 22 of the arm 20. As shown in FIGS. 1 and 3, the connecting end 22 of the arm 20 is fixedly attached to the positioning segment 40 closer to its second end 44 than the first end 42. Preferably, the connecting end 22 of the arm 20 is complementarily received into an indentation (not shown) in the positioning segment 40 and welded thereto. Other methods known in the art can alternatively be used to connect the two components 20, 40.

The detachable securing means preferably comprises a rod 50 having an exterior surface 52, a bottom end 54, and a top end 56. At least a portion of the exterior surface 52 of the rod 50 is of a size to be complementarily received into the bore 46. A portion of the top end 56 of the rod 50 is wider than the bore 46 and, as shown in FIG. 1, the top end 56 preferably flares out to form a gripping surface for the surgeon to twist the rod 50, so that the rod 50 resembles a finger screw.

As best shown in FIG. 4A, the mounting member 30 defines a passage 38 through at least a portion thereof. The passage 38 is of a size to complementarily receive a portion of the rod 50 adjacent its bottom end 54. The passage 38 and portion of the exterior surface 52 of the rod 50 adjacent its bottom end 54 preferably have complementary threaded surfaces. Thus, the rod 50 is movable within the passage 38 by rotating the rod 50 relative to the mounting member 30.

Of note, in the preferred embodiment, the threaded section 47 of the bore 46 of the positioning segment 40 is also threaded with a surface complementary to the threaded surface of the rod 50, e.g., the threaded section 47 of the bore 46 and the threaded portion of the passage 38 have an identical surface, both of which engage the threaded portion of the bottom end 54 of the rod 50 at different times.

The positioning segment 40 can be placed in one of two operative positions relative to the mounting member 30, namely, an engaged position and a released position. The positioning segment 40, however, can be in different radial positions relative to the mounting member when in these two positions. In the engaged position which is best shown in FIG. 1, the rod 50, when disposed through the bore 46 of the positioning segment 40, is positioned within the passage 38 a desired depth so that a portion of the top end 56 of the rod 50 contacts a portion of the second end 44 of the positioning segment 40. Concurrently, the first end 42 of the positioning segment 40 contacts the engaging surface 36 of the mounting member 30 so that the positioning segment 40 is held between the mounting member 30 and the top end 56 of the rod 50. In the released position, the top end 56 of the rod 50 is spaced apart from the second end 44 of the positioning segment 40 so that the positioning segment 40 is rotatable from one desired radial position to another desired radial position.

In use, the positioning segment 40 starts at the released position. The rod 50 is disposed through the bore 46 and maintained in the bore 46 by the threaded section 47 of the bore 46. That is, the threaded portion of the rod 50 adjacent its bottom end 54 is moved through the complementarily threaded section 47 of the bore 46 by screwing the rod 50 relative to the positioning segment 40. After traversing through the threaded section 47, the rod 50 is captured in the bore 46 by the top end 56 of the rod 50, which is wider than the bore 46 and the threaded section 47. Thus, the captured rod 50 may only be extracted by relative twisting motion and pulling upward on the rod 50. As shown best in FIG. 3, the diameter of the bore 46 preferably increases below the threaded section 47, allowing the rod 50 to move freely while captured in the bore 46. This means of capturing the rod 50 within the bore 46 prevents the rod 50 from inadvertently falling out of the bore 46, which is a significant concern in a surgical procedure.

The bottom end 54 of the rod 50, after being captured in the bore 46, can freely slide to the second end 44 of the positioning segment 40 to be stationarily positioned relative to the mounting member 30, e.g., partially screwed into the threaded portion of the passage 38. Since the positioning segment 40 is in the released position when the bottom end 54 of the rod 50 initially enters into the passage 38, the top end 56 of the rod 50 does not contact the second end 44 of the positioning segment 40 and the positioning segment 40 can be rotated about the rod 50. That is, the rod 50 is disposed through the bore 46 (which extends along the axis of rotation R) so that the rod 50 rotatably aligns the positioning segment 40 relative to the axis of rotation R as the positioning segment 40 rotates. Once the positioning segment 40 is at the desired radial position, the rod 50 is then twisted father into the passage 38 of the mounting member 30. When the rod 50 is sufficiently tightened so that the top of the rod 50 contacts the second end 44 of the positioning segment 40, then the positioning segment 40 is in the engaged position.

Additionally, the detachable securing means preferably further comprises a means for locking the positioning segment 40 at the selected desired radial position when in the engaged position. The preferred locking means comprises the first end 42 of the positioning segment 40 having a non-planar surface and the engaging surface 36 of the mounting member 30 having a complementary non-planar surface. Thus, when the non-planar surfaces of the positioning segment 40 and the mounting means contact each other when in the engaged position, they prevent radial movement between the positioning segment 40 and the mounting member 30.

As shown in FIGS. 1, 3, 4A, and 4B, the preferred embodiment of the non-planar surfaces of the mounting means and positioning segment 40 each have a repeating pattern of radially-extending substantially triangular peaks 60 and valleys 62. Since the triangular peaks 60 and valleys 62 are of a complementary size on the two non-planar surfaces, e.g., each peak and valley are the same dimension, the non-planar surfaces matingly engage and lock with each other. As one skilled in the art will appreciate, the dimensions of the peaks 60 and valleys 62 are proportional to the number of selected radial positions that the positioning segment 40 can be placed, e.g., the wider the peaks 60 and valleys 62, the fewer radial positions that the positioning segment 40 can be locked into placed. Another consideration is that sufficient surface area of the complementary peaks 60 and valleys 62 should exist so that the frictional engagement is strong enough to prevent radial slippage between the non-planar surfaces.

Other embodiments of the locking means are also contemplated. One embodiment comprises the mounting member 30 having at least one cleat (not shown) and the first end 42 of the positioning segment 40 defining a plurality of slots (not shown) therein, or vice versa. Each slot is of a size to complementarily receive one cleat. The slots are disposed radially about the axis of rotation R so that at least one of the slots engages one cleat at each of the desired radial positions. Other contemplated examples of the locking means include the non-planar surfaces having complementary knurled surfaces (not shown) or having complementary detents and interfacing protrusions (not shown). As those skilled in the art will appreciate, the embodiments of the locking means preferably are constructed to allow the positioning segment 40 to be disposed at numerous desired radial positions relative to the mounting member 30.

The present invention is ideal for use in heart surgery, either conventional open heart surgery or by minimally invasive surgery, e.g., minimally invasive coronary artery bypass grafting. For minimally invasive surgery, access to the heart may be achieved through the ribs of the patient using a rib retractor 72. Rib retractors 72, as shown in FIGS. 1, 2, and 5, are adapted to contact a person's adjacent ribs through an incision and separate the ribs apart from each other. A rib retractor 72 can be used, for example, in a thoracotomy incision or used as a sternal retractor for maintaining thoracic cavity access via a sternotomy incision.

In a thoracotomy procedure, the surgeons will typically access the heart via the fourth intercostal space located between the third and fourth ribs, but this may be changed based on the individual patient's anatomy. The rib retractor 72 uses a pair of blades 74 that longitudinally move relative to each other along a rack 76. Each blade is adapted to contact one rib in the subject person. The blades 74 are secured at selected points along the length of the rack 76 as the blades 74 longitudinally move relative to each other. Thus, once the blades 74 are separated a desired distance, the blades 74 are locked in that position and then the surgeon can perform the surgical procedure, such as coronary artery bypass surgery, mitral valve replacement, or the like.

Since the minimally invasive procedure is sometimes performed on a beating heart, it is advantageous to stabilize the heart in the area that the surgical procedure will occur. As shown in FIGS. 1 and 2, an example of such a surgical instrument 80 is a stabilizer 82, described in co-pending application 08/719,354, which is incorporated herein by reference. The stabilizer 82 has a bifurcated member 84 having two prongs 86, a handle segment 89, and a means for connecting the handle segment 89 to the bifurcated member 84. Each prong 86 of the bifurcated member 84, which is also known as a tine assembly, has a first section 87 and a second section 88. The first section 87 is located adjacent the handle segment 89 and terminates in the second section 88. The second section 88 engages the heart or other organ on which the surgical procedure occurs. The handle segment 89 is used to extend the bifurcated member 84 into the chest of the patient to reach the surface of the heart. When the second section 88 engages the heart, the surgeon applies a slight compressive force on the heart in the area that the surgical procedure will occur so that the heart's movement at that specific area is diminished and stabilized. Stabilizing the heart is particularly useful for a heart suturing technique in the area of the coronary arteries such as the anastomosis of a bypass graft.

In the stabilizer embodiment shown, the connecting means pivotally and rotatably couples the bifurcated member 84 to the handle segment 89 using a ball 90 and socket 92. The ball 90 is placed adjacent the lower end of the handle segment 89 in an opening and a portion of the ball 90 is fixedly attached to the bifurcated member 84 so that the bifurcated member 84 is rotatably and pivotally movable relative to the handle segment 89. The ball 90 and attached bifurcated member 84 can be locked in a desired position relative to the handle segment 89. A shaft 94 disposed within the handle segment 89 has an attached socket 92 that contacts the ball 90 as the shaft 94 moves downwardly. The socket 92 detachably engages the ball 90 to frictionally hold the ball 90 in the desired position, which is preferably set after the bifurcated member 84 is disposed on the heart and the attached handle segment 89 oriented to the desired orientation. Moving the shaft 94 the opposite direction disengages the socket 92 from the ball 90, allowing the ball 90 to rotate and pivot relative to the handle segment 89.

Thus, the second sections 88 can be disposed at a predetermined location on the heart and the bifurcated member 84 disposed in a desired position relative to the handle segment 89, such as the handle segment 89 being oriented to a position that does not interfere with the surgeon performing the surgical procedure. The present invention, to which the handle segment 89 is connected, complements the freedom of movement. The surgical instrument 80 can be placed on the body portion 26 of the arm 20 either before or after the positioning segment 40 is in the engaged position, depending on the surgical procedure and the surgeon's preference.

To connect the handle segment 89 to the arm 20, the present invention preferably further comprises a means for movably mounting the handle segment 89 to the arm 20 to assist in connecting the surgical instrument 80. Referring a gain to FIGS. 1 and 2, it is preferred that the mounting means comprises a swivel head 100 having a first portion 102, a second portion 104, and a tightening portion 106. The firs t portion 102 defines a slot 103 therethrough which is of a size to slidably and adjustably receive a portion of the handle segment 89 therein. The handle segment 89, accordingly, is movable in the slot 103 longitudinally and rotationally relative to the first portion of the swivel head.

The second portion 104 defines an opening 105 therethrough which is adapted to detachably and slidably engage the arm 20. The second portion 104 allows slidable movement of the handle segment 89 and attached bifurcated member 84 along the arm 20. The second portion 104 is also pivotal transversely relative to the longitudinal axis of the arm 20. The handle segment 89 thus is movable to any position except where the swivel head 100, handle segment 89, or bifurcated member 84 are blocked by an obstruction, such as a portion of the rib retractor 72. However, since the arm 20 can rotate relative to the mounting member 30, this freedom of movement, coupled with the movement that the ball and socket connecting means and first portion 102 provides, allow the surgeon the greatest flexibility to dispose the second section 88 of each prong on the heart while the handle segment 89 is movably connected to the arm 20. The prior art does not provide equivalent flexibility, making the present invention valuable for use in surgical procedures.

The present invention also allows the handle segment 89 and bifurcated member 84 to be pre-aligned so that the bifurcated member 84 is self-positioning on the patient's heart by lowering the positioning segment 40 and connected arm 20, to which the handle segment 89 is attached. Once the surgeon lowers the bifurcated member 84 to the desired position, the surgeon can then maintain the second sections 88 engaging the heart while rotating the arm 20 and attached handle segment 89, if required, to a position that allows the greatest access to the surgery site. When the arm 20 and handle segment 89 are at the desired orientation, the positioning segment 40 is placed in the engaged position. Either before or after this step, the tightening portion 106 of the swivel head 100 is tightened, preferably by a single turn of the tightening portion 106, to secure the handle segment 89 at a desired position.

The tightening portion 106 of the swivel head 100 operates by a screw member 108 disposed through a section of the swivel head 100 tightening the first and second portions 102, 104 in place. Thus, the tightening portion 106 detachably secures the handle segment 89 at a desired orientation in the slot 103 of the first portion 102 and the swivel head 100 at a desired position on the rib retractor 72 so that the surgeon is free to perform the surgical procedure. The tightened portion 106 can be easily loosened, when desired, to allow the handle segment 89 and the bifurcated member 84 to be moved or slid along the arm 20.

The handle segment 89 thus is held in the desired position by the arm 20 that is connected to the rib retractor 72 used to preform the surgical procedure. As one skilled in the art will appreciate, there are numerous other options available to mount the handle segment 89 to the arm 20 so that the second section 88 is maintained at a desired position. One example of such a mounting means is a ball and socket connection (not shown). For other surgical instruments 80 used with the present invention, a different mounting means may be more appropriate.

As one skilled in the art will appreciate, the present invention can be used in surgical procedures other than heart surgery, including, for example, soft tissue procedures such as vascular thrombosis repair, intestinal resection and anastomosis and other intra-abdominal procedures, and the like.

Although the present invention has been described with reference to specific details of certain embodiments thereof, it is not intended that such details should be regarded as limitations upon the scope of the invention except as and to the extent that they are included in the accompanying claims.

What is claimed is:

1. An apparatus for mounting a surgical instrument to a stationary member, comprising:
   a. an arm adapted to support the surgical instrument thereon and having a connecting end and an opposed free end;
   b. a mounting member fixedly attached to the stationary member; and
   c. means, attached to the connecting end of said arm, for coupling said arm to said mounting member so that said arm is rotatable to a selected one of a plurality of desired radial positions relative to said mounting member and is detachably coupled to said mounting member in the desired radial position, wherein said coupling means comprises:
      i. a positioning segment having a first end adapted to be disposed adjacent said mounting member, an opposite second end, and an axis of rotation about which said positioning segment is rotatable, wherein a portion of said positioning segment is attached to the connecting end of said arm; and ii. means for detachably securing said positioning segment to said mounting member in the desired radial position.

2. The apparatus of claim 1, wherein said positioning segment defines a bore extending along said axis of rotation, and wherein said detachable securing means comprises a rod having an exterior surface, a bottom end, and a top end, at least a portion of said exterior surface being of a size to be complementarily received into said bore and at least a portion of said top end being of a size wider than said bore.

3. The apparatus of claim 2, wherein said mounting member defines a passage through at least a portion thereof, said passage being of a size to complementarily receive a portion of said rod adjacent the bottom end thereof, wherein said passage and a portion of the exterior surface of said rod have complementary threaded surfaces so that said rod is movable within said passage so that said positioning segment is in a selected one of an engaged position, in which, when said rod is disposed through the bore of said positioning segment, said rod is disposed within said passage a desired depth so that a portion of the top end of said rod contacts a portion of the second end of said positioning segment while said first end of said positioning segment concurrently contacts said mounting member, or a released position, in which the top end of said rod is spaced apart from the second end of said positioning segment so that said positioning segment is rotatable from one desired radial position to another desired radial position.

4. The apparatus of claim 3, wherein said detachable securing means further comprises means for locking said positioning segment at the selected desired radial position when in the engaged position.

5. The apparatus of claim 4, wherein said locking means comprises the bottom end of said positioning segment having a non-planar surface and the mounting member having a complementary non-planar surface so that when the non-planar surfaces of said bottom end and said mounting member contact when in the engaged position, the complementary non-planar surfaces prevent radial movement therebetween.

6. The apparatus of claim 5, wherein the non-planar surface of the bottom end of said positioning segment and said mounting member is a plurality of alternating peaks and valleys.

7. The apparatus of claim 3, further comprising means for capturing a portion of said rod within the bore of said positioning segment.

8. The apparatus of claim 7, wherein said capture means comprises a section of the bore of said positioning segment being threaded adjacent the second end thereof, the threaded section complementary to the threaded portion of the exterior surface of said rod adjacent the bottom end thereof, and a portion of said bore adjacent the first end thereof being wider than the threaded section to allow slidable motion of the bottom end of said rod therealong.

9. An apparatus, comprising:

a. an arm adapted to support a surgical instrument thereon and having a connecting end and an opposed free end;

b. a mounting member fixedly attached to a stationary member;

c. a positioning segment having a first end adapted to be disposed adjacent said mounting member, an opposite second end, and an axis of rotation about which said positioning segment is rotatable, wherein a portion of said positioning segment is attached to the connecting end of said arm so that said arm is rotatable to a selected one of a plurality of desired rotational positions relative to said mounting member; and d. means for detachably securing said positioning segment to said mounting member in the desired rotational position so that said arm is detachably coupled to said mounting member in the desired rotational position.

10. The apparatus of claim 9, wherein said positioning segment defines a bore extending along said axis of rotation, and wherein said detachable securing means comprises a rod having an exterior surface, a bottom end, and a top end, at least a portion of said exterior surface being of a size to be complementarily received into said bore and at least a portion of said top end being of a size wider than said bore.

11. The apparatus of claim 10, wherein said mounting member defines a passage through at least a portion thereof, said passage being of a size to complementarily receive a portion of said rod adjacent the bottom end thereof, wherein said passage and a portion of the exterior surface of said rod have complementary surfaces so that said rod is movable within said passage so that said positioning segment is in a selected one of an engaged position, in which, when said rod is disposed through the bore of said positioning segment, said rod is disposed within said passage a desired depth so that a portion of the top end of said rod contacts a portion of the second end of said positioning segment while said first end of said positioning segment concurrently contacts said mounting member, or a released position, in which the top end of said rod is spaced apart from the second end of said positioning segment so that said positioning segment is rotatable from one desired rotational position to another desired rotational position.

12. The apparatus of claim 11, wherein said detachable securing means further comprises means for locking said positioning segment at the selected desired rotational position when in the engaged position.

13. The apparatus of claim 12, wherein said locking means comprises the bottom end of said positioning segment having a non-planar surface and the mounting member having a complementary non-planar surface so that when the non-planar surfaces of said bottom end and said mounting member contact when in the engaged position, the complementary non-planar surfaces prevent rotational movement therebetween.

14. An apparatus, comprising:

a. an arm adapted to support a surgical instrument thereon and having a connecting end and an opposed free end;

b. a mounting member fixedly attached to a stationary member;

c. a positioning segment having a first end adapted to be disposed adjacent said mounting member, an opposite second end, and an axis of rotation about which said positioning segment is rotatable, said positioning segment defining a bore extending along said axis of rotation wherein a portion of said positioning segment is attached to the connecting end of said arm so that said arm is rotatable to a selected one of a plurality of desired rotational positions relative to said mounting member; and d. a rod having an exterior surface, a bottom end, and a top end, at least a portion of said exterior surface being of a size to be complementarily received into the bore of said positioning segment and at least a portion of said top end being of a size wider than said bore, wherein said mounting member defines a passage through at least a portion thereof, said passage being of a size to complementarily receive a portion of said rod adjacent the bottom end thereof, wherein said passage and a portion of the exterior surface of said rod have complementary surfaces so that said rod is movable within said passage so that said positioning segment is in a selected one of an engaged position, in which, when said rod is disposed through the bore of said positioning segment, said rod is disposed within said passage a desired depth so that a portion of the top end of said rod contacts a portion of the second end of said positioning segment while said first end of said positioning segment concurrently contacts said mounting member, or a released position, in which the top end of said rod is spaced apart from the second end of said positioning segment so that said positioning segment is rotatable from one desired rotational position to another desired rotational position.

15. The apparatus of claim 14, wherein said positioning segment and said mounting means further comprise means for locking said positioning segment at the selected desired rotational position when in the engaged position.

16. The apparatus of claim 15, wherein said locking means comprises the bottom end of said positioning segment having a non-planar surface and the mounting member having a complementary non-planar surface so that when the non-planar surfaces of said bottom end and said mounting member contact when in the engaged position, the complementary non-planar surfaces prevent rotational movement therebetween.

* * * * *